(12) United States Patent
Lin et al.

(10) Patent No.: US 6,395,726 B1
(45) Date of Patent: May 28, 2002

(54) 3,6-DISUBSTITUTED PENAM SULFONE DERIVATIVES

(75) Inventors: Yang-I. Lin, Tappan; Panayota Bitha, Nanuet; Zhong Li, Congers; Gerardo D. Francisco, Orangeburg, all of NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/489,623

(22) Filed: Jan. 24, 2000

Related U.S. Application Data

(60) Provisional application No. 60/150,706, filed on Jan. 26, 1999.

(51) Int. Cl.[7] ............................................. A01N 43/00
(52) U.S. Cl. .................................. 514/210.05; 540/310
(58) Field of Search ...................... 514/210.05; 540/310

(56) References Cited

U.S. PATENT DOCUMENTS

| | | | |
|---|---|---|---|
| 4,234,579 A | 11/1980 | Barth | 424/246 |
| 4,287,181 A | 9/1981 | Kellogg | 424/114 |
| 4,503,040 A | 3/1985 | Barth | 424/114 |
| 4,562,073 A | 12/1985 | Micetich et al. | 424/114 |
| 4,591,459 A | 5/1986 | Barth | 260/245.2 |
| 5,637,579 A | 6/1997 | Hubschwerlen et al. | 514/192 |

FOREIGN PATENT DOCUMENTS

| | | |
|---|---|---|
| EP | 0041047 | 12/1981 |
| EP | 0083977 | 7/1983 |

OTHER PUBLICATIONS

Fessenden, R.J. and Fessenden, J.S., "Organic Chemistry", 1982, Willard Grant Press, Boston, p. 451.*
Hawley, Gessner, "The Condensed Chemical Dictonary", 1977, Van Nostrand, New York, p. 436.*
Streitwieser, A. and Heathcock, C.H., "Introduction to Organic Chemistry, 2nd Ed.", Macmillan, New York, 1981, p. 1061.*
Panayota Bitha et al, 6–(1–Hydroxyalykyl)Penam Sulfone Derivatives as Inhibitors of Class 1 and Class C β–Lactamases II, Bioorganic & Medicinal Chemistry Letters 9 (1999) 997–1002.

* cited by examiner

Primary Examiner—Mukund J. Shah
Assistant Examiner—Thomas McKenzie
(74) Attorney, Agent, or Firm—John W. Hogan, Jr.

(57) ABSTRACT

Compounds are provided having the following formulae I and II:

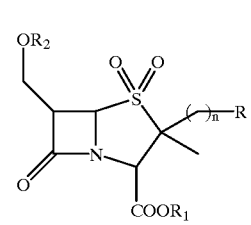

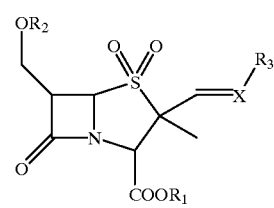

wherein n is 0 or 1 and when n=1, R is a 5 or 6 membered heterocyclic ring, hydroxy, halogen, oxo, carbamoyl, alkoxy, or disubstituted amino, when n=0, R is an ester, cyano or amide group;

X is CH or NH;

$R_3$ is cyano, methoxy, or acetamido;

$R_1$ is hydrogen, alkyl, a negative charge, a cation selected from the group consisting of sodium, potassium and tetraalkylammonium and acyloxyalkyl, or alkoxycarbonyloxyalkyl; and $R_2$ is hydrogen, acyl, trisubstituted silyl carbamoyl or an amino acid residue; or pharmaceutically acceptable salts thereof.

8 Claims, No Drawings

3,6-DISUBSTITUTED PENAM SULFONE DERIVATIVES

This application claims the benefit of U.S. Provisional Application No. 60/150,706, now abandoned which was converted from U.S. patent application Ser. No. 09/237,726, filed Jan. 26, 1999, pursuant to a petition filed under 37 C.F.R. 1.53(c)(2)(i).

FIELD OF INVENTION

The present invention is directed to β-lactamase inhibitors useful in combination with β-lactam antibiotics. More specifically, the present invention is directed to novel 3,6-disubstituted penam sulfone derivatives which demonstrate potent β-lactamase inhibitory activity.

BACKGROUND OF THE INVENTION

Penicillins and cephalosporins are the most frequently and widely used β-lactam antibiotics. However, the development of bacterial resistance to these antibiotics has had a damaging effect on maintaining the effective treatment of bacterial infections.

The most significant, known mechanism related to the development of bacterial resistance to the β-lactam antibiotics is the production of Class A and Class C serine β-lactamases. These β-lactamases compounds degrade the β-lactam antibiotics, resulting in a loss of antibacterial activity. It is known that Class A serine β-lactamases, which have molecular weights of about 29 kDa, preferentially hydrolyze penicillins, whereas Class C serine β-lactamases which have molecular weights of about 39 kDa, preferentially hydrolyze cephalosporins. Bacterial resistance to these antibiotics could be greatly reduced by administering the β-lactam antibiotic in combination with a compound which inhibits these enzymes.

A number of β-lactamase inhibitors are known in the art. For example, U.S. Pat. No. 4,234,579 discloses penicillanic acid 1,1-dioxide (i.e., Sulbactam) useful for enhancing the activity of a number of β-lactam antibiotics. U.S. Pat. No. 4,562,073 discloses a penicillin derivative (Tazobactam) useful as a β-lactamase inhibitor. Likewise, U.S. Pat. Nos. 4,287,181 and 5,637,579 disclose penicillanic acid derivatives useful in enhancing the effectiveness of β-lactam antibiotics. However, the compounds disclosed in these patents are active only towards Class A serine β-lactamases and demonstrate poor activity against Class C serine β-lactamases.

Two positions can be modified in the penam sulfone base structure: the 3 β-methyl group and the 6-position. In the compounds discussed above, only one of the 3 or 6 positions is modified. Thus far, such a singular modification on the penam sulfone structure has not produced the desired activity against both Class A and Class C serine β-lactamases. Accordingly, it can be seen that there is a need for compounds having such dual activities.

SUMMARY OF THE INVENTION

The present invention provides compounds having β-lactamase inhibitory activity against both Class A and Class C serine β-lactamases.

The present invention is directed to compounds of the following formulae I and II:

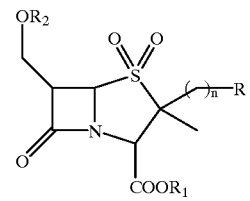

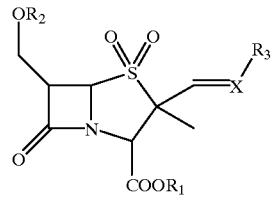

wherein
n is 0 or 1 and
when n=1, R is a 5 or 6 membered heterocyclic ring, hydroxy, halogen, oxo, carbamoyl, alkoxy, disubstituted amino, or
when n=0, R is an ester, cyano or amide group;
X is CH or NH;
$R_3$ is cyano, methoxy or acetamido; and
$R_1$ is hydrogen, alkyl, a negative charge, a cation selected from the group consisting of sodium, potassium and tetraalkylammonium and acyloxyalkyl, or alkoxycarbonyloxyalkyl; and
$R_2$ is hydrogen, acyl, trisubstituted silyl carbamoyl or an amino acid residue; or pharmaceutically acceptable salts thereof.

DETAILED DESCRIPTION OF THE INVENTION

Preferably, the compounds of the present invention are those of the formula set forth above where n is 1 and R is 1,2,3-triazole, isoxazole, imidazole or pyridine; $R_1$ is sodium; and $R_2$ is hydrogen; or pharmaceutically acceptable salts thereof.

Most preferably, the compounds of the present invention are:

(2S,3S,5R, 6R)-6-Hydroxymethyl-3-methyl-4,4,7-trioxo-3-[1,2,3]triazol-1-ylmethyl-4-lambda(6)-thia-1-aza-bicyclo[3.2.0]heptane-2-carboxylic acid;

(2S,3R,5R,6R)-6-Hydroxymethyl-3-(methoxyimino-methyl)-3-methyl-4,4,7-trioxo-4-lambda(6)-thia-1-aza-bicyclo[3.2.0]heptane-2-carboxylic acid;

(Z)-(2S,3S,5R,6R)-6-Hydroxymethyl-3-methyl-3-(3-nitrilo-propenyl)-4,4,7-trioxo-4-lambda(6)-thia-1-azabicyclo[3.2.0]heptane-2-carboxylic acid; or (E)-(2S,3S,5R,6R)-6-Hydroxymethyl-3-methyl-3-(3-nitrilo-propenyl)-4,4,7-trioxo-4-lambda(6)-thia-1-aza-bicyclo[3.2.0]heptane-2-carboxylic acid.

As used herein the terms "alkyl" and "alkoxy" are used to represent straight or branched carbon chains of 1–6 atoms. The term "halogen" is used to represent chlorine, bromine, fluorine and iodine.

The compounds of the present invention may also be used in the form of a pharmaceutically acceptable acid addition salt having the utility of the free base. Such salts, prepared by methods well known in the art, may be formed with both inorganic or organic acids, e.g., fumaric, benzoic, maleic, ascorbic, pamoic, succinic, bismethylenesalicylic, methanesulfonic, ethanolsulfonic, acetic, oxalic, propionic, tartaric, salicylic, citric, gluconic, lactic, malic, mandelic, annamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids.

The compounds of the present invention may be prepared by any suitable method which will be recognized by those skilled in the art. However, the present compounds may be advantageously prepared according to the Schemes set forth below.

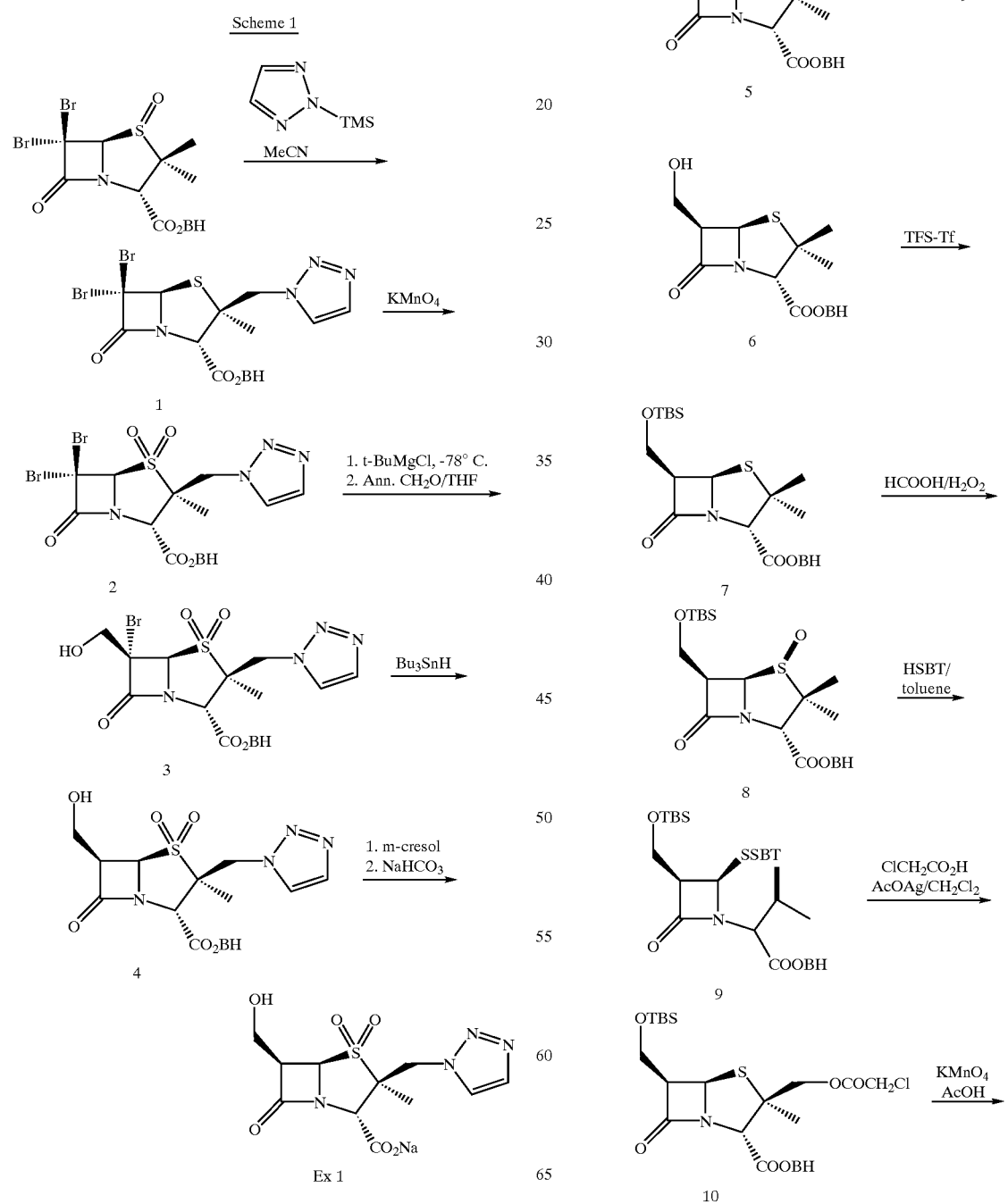

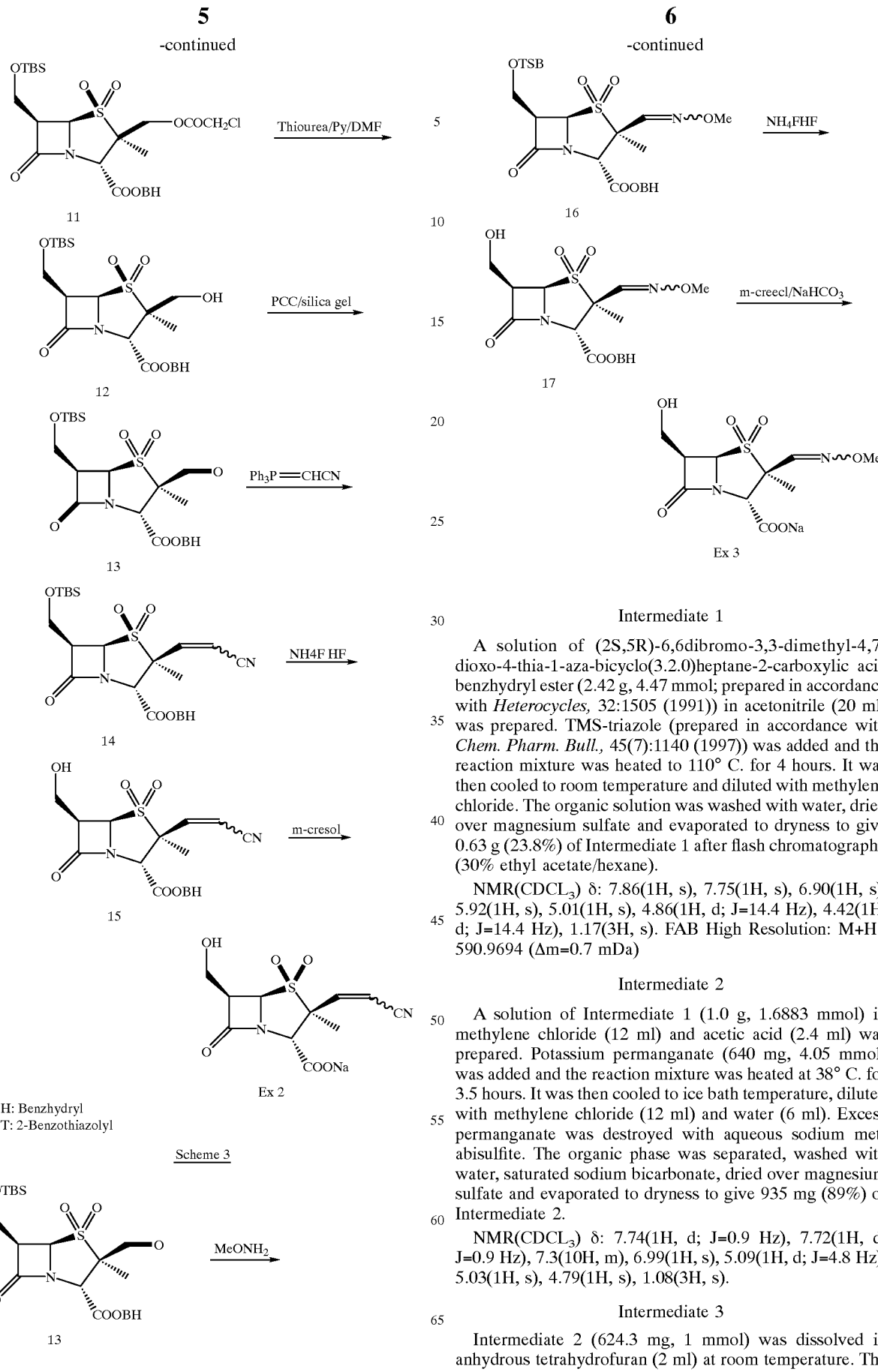

BH: Benzhydryl
BT: 2-Benzothiazolyl

Scheme 3

Intermediate 1

A solution of (2S,5R)-6,6dibromo-3,3-dimethyl-4,7-dioxo-4-thia-1-aza-bicyclo(3.2.0)heptane-2-carboxylic acid benzhydryl ester (2.42 g, 4.47 mmol; prepared in accordance with *Heterocycles*, 32:1505 (1991)) in acetonitrile (20 ml) was prepared. TMS-triazole (prepared in accordance with *Chem. Pharm. Bull.*, 45(7):1140 (1997)) was added and the reaction mixture was heated to 110° C. for 4 hours. It was then cooled to room temperature and diluted with methylene chloride. The organic solution was washed with water, dried over magnesium sulfate and evaporated to dryness to give 0.63 g (23.8%) of Intermediate 1 after flash chromatography (30% ethyl acetate/hexane).

NMR(CDCL$_3$) δ: 7.86(1H, s), 7.75(1H, s), 6.90(1H, s), 5.92(1H, s), 5.01(1H, s), 4.86(1H, d; J=14.4 Hz), 4.42(1H, d; J=14.4 Hz), 1.17(3H, s). FAB High Resolution: M+H= 590.9694 (Δm=0.7 mDa)

Intermediate 2

A solution of Intermediate 1 (1.0 g, 1.6883 mmol) in methylene chloride (12 ml) and acetic acid (2.4 ml) was prepared. Potassium permanganate (640 mg, 4.05 mmol) was added and the reaction mixture was heated at 38° C. for 3.5 hours. It was then cooled to ice bath temperature, diluted with methylene chloride (12 ml) and water (6 ml). Excess permanganate was destroyed with aqueous sodium metabisulfite. The organic phase was separated, washed with water, saturated sodium bicarbonate, dried over magnesium sulfate and evaporated to dryness to give 935 mg (89%) of Intermediate 2.

NMR(CDCL$_3$) δ: 7.74(1H, d; J=0.9 Hz), 7.72(1H, d; J=0.9 Hz), 7.3(10H, m), 6.99(1H, s), 5.09(1H, d; J=4.8 Hz), 5.03(1H, s), 4.79(1H, s), 1.08(3H, s).

Intermediate 3

Intermediate 2 (624.3 mg, 1 mmol) was dissolved in anhydrous tetrahydrofuran (2 ml) at room temperature. The solution was cooled to −78° C. under nitrogen. The 2M t-butyl magnesium chloride solution in ether (550 μl, 1.1 mmol) was added dropwise maintaining the temperature at −78° C. The light yellow solution was stirred at −78° C. for 45 minutes and the cold anhydrous formaldehyde solution in THF (excess) was added maintaining the temperature below 66° C. Stirring continued for 30 minutes at −78° C. and the solution was quenched with HOAc (57 μl) in THF (0.5 ml). The reaction mixture was allowed to warm to room temperature, then was diluted with ethyl acetate and filtered. The filtrate was evaporated to dryness to give after flash chromatography (50% ethyl acetate/hexane) 165 mg (28.7%) of Intermediate 3.

NMR(CDCL$_3$) δ: 7.73(1H, s), 7.70(1H, s), 7.38(10H, m), 6.99(1H, s), 5.13(2H, q), 4.84(1H, s), 4.81(1H, s), 4.18(1H, m), 4.71(1H, m), 2.52(1H, q, OH), 1.08(3H, s).

FAB High Resolution: M+H=575.0609 (Δm=−0.9 mDa).

Intermediate 4

Intermediate 3 (513 mg, 0.892 mmol) was dissolved in methylene chloride (5 ml). 1,1'-Azabis (cyclohexanecarbonitrile) (5 mg) and tributyltin hydride (240 μl, 0.892 mmol) were added and the reaction mixture was refluxed for 30 minutes and then evaporated to dryness to give, after flash chromatography, 344 mg (78%) of Intermediate 4.

NMR(CDCL$_3$) δ: 7.71(2H, d; J=3.18 Hz), 7.38(10H, m), 6.98(1H, s), 5.12(2H, q), 4.71 (1H, s), 4.70(1H, d; J=4.6 Hz), 4.25(3H, m), 2.10(1H, OH), 1.06(3H, s). ESI MS: 497.3 (M+H).

EXAMPLE 1

A solution of Intermediate 4 (298.5 mg, 0.6 mmol) in m-cresol (1.8 ml) was prepared and heated at 47° C. for 3.5 hours. It was then cooled to room temperature, diluted with ether, filtered and washed with ether. The solid material was then dissolved in water (5 ml) containing sodium bicarbonate (50.4 mg) and filtered. The filtrate was washed with ether and freeze-dried to give 109 mg (51.5%) of product as a white solid.

NMR(D$_2$O) δ: 8.12(1H, s), 7.85(1H, s), 5.37(1H, d; J=15.4 Hz), 5.16(1H, d; J=15.4 Hz), 5.08(1H, d; J=4.6 Hz), 4.57(1H, s), 4.38–4.31(1H, m), 4.28–3.98(2H, m), 1.41(3H, s).

Intermediate 5

A solution of (2S,5R)-6,6-dibromo-3,3-dimethyl-7-oxo-4-thia-1-azabicyclo(3.2.0)heptane-2-carboxylic acid benzhydryl ester (10.0 g; 0.019 mole; prepared in accordance with *J. Org. Chem.*, 52:3659 (1987)) in anhydrous THF (60 ml) was prepared under nitrogen and cooled to −77° C. To the cold solution was added with good stirring 2M t-butyl magnesium chloride in an ether solution (11 ml; 0.0209 mol) in such rate that the internal temperature remained under −65° C. The cold reaction mixture was stirred for 45 minutes. To this solution was then added via syringe a cold dry monomeric formaldehyde solution in anhydrous THF (100 ml) maintaining the temperature below −65° C. The monomeric formaldehyde/THF solution was prepared as follows: Paraformaldehyde (30 g. 1.0 mol) and p-toluenesulfonic anhydride (4.9 g, 15 mmol) were placed in a three-necked flask, and tetrahydrofuran (1.0 L) was added thereto. The mixture was heated and a slow distillation of the solvent was maintained. Under a weak stream of nitrogen, a solution of anhydrous monomeric formaldehyde in THF was collected in a dry flask maintained at −78° C. The solution was stored at −78° C. The reaction mixture was finally stirred at −77° C. for 30 minutes and quenched with glacial acetic acid (1.2 ml) in THF (10 ml).

The reaction mixture was allowed to warm to room temperature and was diluted with ethyl acetate (100 ml) and water (50 ml). The organic phase was removed, washed with water, dried over sodium sulfate and evaporated to dryness to give, after flash column chromatography (30% Ethyl Acetate/Hexanes), 3.2 g. (36%) of Intermediate 5 as a mixture of α,β isomeric alcohols (75% β and 25% α). β-alcohol: NMR(CDCL$_3$) δ: 7.31 (10H, m), 6.93 (1H, s), 5.56 (1H, s), 4.61 (1H, s), 4.23–4.06 (2H, m), 2.25 (1H, t, OH),1.58 (3H, s), 1.26 (3H, s). α-alcohol: NMR(CDCL$_3$) δ: 7.33 (10H, m), 6.98 (1H, s), 5.66 (1H, s), 4.56 (1H, s), 4.27–4.06 (2H, m), 2.24 (1H, t, OH),1.58 (3H, s), 1.29 (3H, s).

High Resolution MS: Calcd. for M+H=476.0531, measd.=476.0351 (Δm=0.0 mDa).

Intermediate 6

To a solution of Intermediate 5 (12.7 g; 26.65 mmol) in anhydrous methylene chloride (160 ml) under nitrogen tributyl tin hydride (7.16 ml; 26.65 mmol) and 1,1'-Azabis (cyclohexanecarbonitrile) (159 mg) were added. The resulting solution was refluxed for two hours and then evaporated to dryness. Oily residue was treated with 50% ethyl acetate/ Hexanes and the crystals isolated by filtration to give 9.8 g (92.9%) of Intermediate 6.

NMR(CDCL$_3$) δ: 7.35(10H, m), 6.92(1H, s), 5.5(1H, d; J=4.3 Hz). EI HIGH RESOLUTION 397.1341

Intermediate 7

A solution of Intermediate 6 (11.5 g; 28.9 mmol) in anhydrous methylene chloride (290 ml) was cooled to −20° C. under nitrogen. Hunig's base (7.2 ml; 41.3 mmol) was added followed by addition of t-butyl-dimethylsilyl triflate (8.6 ml; 37.5 mmol). The resulting light yellow solution was stirred at −20° C. for 30 minutes. It was then washed with two 75 ml portions of water, dried over MgSO$_4$ and evaporated to dryness to give 13.5 g (91.3%) of chromatographed Intermediate 7 (30% Ethyl acetate/Hexanes).

NMR(CDCL$_3$) δ: 7.3(10H, m), 6.93(1H, s), 5.44(1H, d; J=4.2 Hz), 4.44(1H, s),4.09–3.81(3H, m), 1.63(3H, s), 1.25 (3H, s), 0.88(9H, s). CI HIGH RESOLUTION (M+H) 512.2249.

Intermediate 8

Intermediate 7 (1.26 g; 2.246 mmol) was dissolved in methylene chloride (7 ml). Formic acid (88%, 0.36 ml) was added followed by addition of 35% hydrogen peroxide (0.43 ml). The resulting reaction solution was heated at 35° C. for 30 minutes. Water (1.8 ml) was then added and the solution was stirred for another 15 minutes. The organic phase was removed, washed with water, saturated NaHCO$_3$, water and evaporated to dryness to give, after flash chromatography (20% ethyl acetate/Hexanes), 908 mg (70 %) of Intermediate 8 (a mixture of α,β-isomers).

NMR(CDCL$_3$) δ: α-isomer: 7.3(10H, m),6.99(1H, s), 4.69(1H, s), 4.67(1H, d; J=3.9 Hz), 4.4(1H, t; J=7.2 Hz), 4.02(1H, m), 3.91(1H, dd; J=5.4 Hz). β-isomer: 7.35(10H, m), 6.97(1H, s), 4.62(1H, d; J=3.6 Hz), 4.39(1H, s), 4.08 (2H, d; J=4.5 Hz), 3.95(1H, m), 1.4(3H, s), 1.1(3h, s), 0.91(9H, s).

Intermediate 9

A solution of Intermediate 8 (9.65 g, 18.28 mmol) and 2-mercaptobenzothiazole (3.12 g, 18.28 mmol) in anhydrous toluene (64 ml) was heated at reflux for 1.5 hours using a Dean-Stark apparatus. Heating was then removed. The reaction solution was cooled to room temperature and evaporated to dryness to give 12.37 g of Intermediate 9 which was used 'as is' for the next step.

NMR(CDCL$_3$) δ: 7.86–7.20(14H-m), 6.99(1H, s), 5.52 (1H, d; J=5.4 Hz), 5.1 (2H, d; J=14.1), 4.86(1H, s), 4.14(2H, m), 3.78(1H, m), 1.96(3H, s), 0.94(9H, s), 0.08(6H, d).

HIGH RESOLUTION MS: calcd. for M+H=677.1998, measd.: 677.2016 (Δm=1.8 mDa.

Intermediate 10

To a solution of Intermediate 9 (6.1 g; 9.02 mmol) in anhydrous methylene chloride (40 ml) was added silver acetate (3.05 g, 18.17 mmol) followed by a solution of chloroacetic acid (36.6 g; 388 mmol) in anhydrous methylene chloride (94 ml) via addition funnel. The reaction mixture was stirred at room temperature for 48 hours and then filtered through celite. The filtrate was evaporated to dryness and the crude residue was purified by flash chromatography giving 1.5 g (27.7%) of Intermediate 10.

NMR(CDCL$_3$) δ: 7.26(10H, m), 6.86(1H, s), 5.48(1H, d; J=4.1 Hz), 4.71(1H, s), 4.25–3.75(7H, m), 1.2(3H, s), 0.81 (9H, s), 0.015(6H, s).

HIGH RESOLUTION MS: calcd. for M+H=604.1956, measd.=604.1907(Δm=4.9 mDa).

Intermediate 11

A solution of Intermediate 10 (1.5 g; 2.48 mmol) in methylene chloride (12.5 ml) was prepared. To the solution was added acetic acid (3.7 ml) and potassium permanganate (1.05 g, 6.65 mmol). The reaction mixture was stirred at room temperature for 3 hours. The mixture was then cooled in ice bath and the excess potassium permanganate was destroyed with an aqueous solution of sodium metabisulfite. The methylene chloride phase was separated, washed with water, dried over magnesium sulfate and evaporated to dryness. The crude product was purified by flash chromatography (20% ethyl acetate/hexanes) to afford 1.38 g (88%) of Intermediate 11.

NMR(CDCL$_3$) δ: 7.28(10H, m), 6.89(1H, s), 4.67(2H, dd; J=12.0 & 17.4 Hz), 4.54(2H, d; J=12.6 Hz), 4.33(1H, t; J=9.9 Hz), 4.09(1H, m), 4.0(2H, d; J=0.6 Hz), 3.89(1H, dd; J=6.9 & 7.1 Hz), 1.01(3H, s), 0.81(9H, s), 0.08(6H, s).

HIGH RESOLUTION MS: calcd. For M+H=636.1854, measd.=636.1847(Δm=0.7 mDa).

Intermediate 12

A solution of Intermediate 11 (636.24 mg, 1 mmol), and thiourea (229 mg, 3 mmol) in dry DMF (1.2 ml) and anhydrous pyridine (480 µl) was prepared and stirred at room temperature for 3 hours. The resulting suspension was diluted with ethyl acetate, filtered and washed with ethyl acetate. The combined ethyl acetate solutions were evaporated to dryness. The residue was dissolved in methylene chloride and washed with water. The organic phase was dried over magnesium sulfate and evaporated to dryness to give 542 mg, 97% of Intermediate 12 as a white solid.

NMR(CDCL$_3$) δ: 7.27(10H, m), 6.9(1H, s), 5.18(1H, s), 4.48(1H, d; J=4.8 Hz), 4.32(1H, t; J=10.02 & 9.93 Hz), 4.09(1H, m), 4.01 & 3.97(1H, dd; J=3.6 & 3.54 Hz), 3.87(1H, dd; J=7.2 Hz), 3.69(1H, dd; J=10.7 Hz), 2.62(1H, dd; J=3.7 Hz), 0,91(3H, s), 0.81(9H, s).

Intermediate 13

Pyridinium chlorochromate (1.07 g; 4.8 mmol) and silica gel (1.5 g) were slurried in anhydrous methylene chloride (12 ml). To this mixture was added with good stirring a solution of Intermediate 12 (559.7 mg; 1 mmol) in anhydrous methylene chloride (4 ml). The resulting reaction mixture was stirred at room temperature for 16 hours. It was then diluted with methylene chloride, filtered and washed with methylene chloride. The filtrate was washed with 30–50 ml portions of water, dried over magnesium sulfate and evaporated to dryness to give the aldehyde Intermediate 13 (382 mg; 68.4%).

NMR(CDCL$_3$) δ: 9.61(1H, s), 7.25(10H, m), 6.92(1H, s), 5.41(1H, s), 4.58(1H, d; J=4.8 Hz), 4.29(1H, t; J=9.9 Hz), 4.15(1H, m), 3.88(1H, dd; J=7.2 Hz), 1.2(3H, s), 0.81(9H, s).

Intermediate 14

Cyanomethylenetriphenylphosphorane (387.2 mg; 1.286 mmol; prepared in accordance with Chem. Ber., 94:578 (1961) and lithium perchlorate (137.6 mg; 1.29 mmol) were slurried in anhydrous methylene chloride (3.2 ml) at −20° C. To the cold suspension was added dropwise a solution of Intermediate 13 (640 mg; 1.147 ml) maintaining the temperature at −20° C. The cold bath was then removed and the reaction mixture was stirred at room temperature for 5 hours. The resulting green solution was evaporated to dryness and the two isomers were separated by flash column chromatography yielding Intermediate 14 (cis:) 302.2 mg; 45.4% and (trans:) 158 mg; 27.2%).

NMR(CDCL$_3$) δ: cis isomer: 7.36(10H, m), 6.96(1H, s), 6.44(1H, d; J=12.3 Hz), 5.88(1H, d; J=12.2 Hz), 4.9(1H, s), 4.71(1H, d; J=4.9 Hz), 4.39(1H, t; J=9.96 Hz), 4.2(1H, m), 3.96(1H,dd; J=7.26 Hz), 1.66(3H, s), 0.89(9H, s), 0.07(6H, s).

trans isomer: 7.23(10H, m), 6.98(1H, s), 6.77(1H, d; J=16.5 Hz), 5.28(1H, d; J=16.5 Hz), 4.75(1H, s), 4.6(1H, d; J=4.9 Hz), 4.39(1H, t; J=6.9 & 9.99), 4.2(1H, m), 3.95(1H, dd; J=7.29 Hz), 1.22(3H, s), 0.88(9H, s), 0.07(6H, s).

Intermediate 15

Ammonium hydrogen difluoride (106 mg, 1.86 mmol) was added to a solution of Intermediate 15 (cis isomer) (135 mg, 0.2324 mmol) in dry DMF (0.88 ml) and N-methyl-2-pyrrolidinone (0.325 ml). The resulting clear light yellow solution was stirred at room temperature for 5 hours and filtered. The filtrate was evaporated to dryness and chromatographed to give Intermediate 15 (cis isomer) (95 mg, 88%).

NMR(CDCL$_3$) δ: 7.36(10H, m), 6.97(1H, s), 6.5(1H, D; J=12.3 Hz), 5.9(1H,D; J=12.3 Hz), 4.95(1H, s), 4.78(1H, d; J=4.59 Hz), 4.3–4.1(3H, m), 1.6(3H, s).

HIGH RESOLUTION MS: calcld. For M+H=467.1277, measd. :467.1260 (Δm=1.7 mDa).

The same conditions were followed for the preparation of the trans isomer. NMR(CDCL$_3$) δ: 7.3(10H, m), 6.98(1H, s), 6.84(1H, d; J=16.5 Hz), 5.374.84(1H, s), (1H, d; J=16.5 Hz), 4.74(1H, d; J=4.56 Hz), 4.3–4.1(3H, m), 1.2(3H, s).

EXAMPLE 2

A solution of Intermediate 15 (cis isomer) (226 m, 0.4845 mmol) in m-cresol (1.5 ml) was heated for 4 hours at 47° C. and then cooled to room temperature. It was diluted with ether and a solution of sodium bicarbonate (40.7 mg, 0.4845 mmol) was added. The aqueous phase was separated, washed with ether and freeze-dried to give product (123.5 mg, 79%).

NMR(D$_2$O) δ: 6.68(1H, d; J=12.4 Hz), 6.16(1H, d; J=12.4 Hz), 5.25(1H, d; J=4.7 Hz), 4.36(1H, m), 4.22(1H, dd; J−8.73 Hz), 4.08(1H, dd; 8.16 Hz), 1.94(3H, s).

HIGH RESOLUTION MS: calcd. For M−H=299.0338, measd.=299.0343 (Δm=−0.5 mDa).

The same conditions were followed to obtain the trans isomer. NMR(D$_2$O) δ: 7.08(1H, d; J=16.5 Hz), 6.07(1H, d; J=16.5 Hz), 5.2(1H, s), 4.36(1H, m), 4.21(1H, dd; J=8.10 Hz), 4.07(1H, dd; J=8.10 Hz), 1.64(3H, s).

Intermediate 16

A solution of Intermediate 13 (381.5 mg; 0.684 mmol) and methoxylamine hydrochloride (58.3 mg; 0.684 mmol) in anhydrous methylene chloride (1.5 ml) and anhydrous pyridine (83 μl; 1.026 mmol) was stirred at room temperature for 7.5 hours. The reaction mixture was then diluted with methylene chloride and the solution was washed three times with water (40 ml portions). The organic phase was dried over magnesium sulfate and evaporated to dryness to give, after flash column chromatography (20% ethyl acetate/hexanes), 192 mg of Intermediate 16 in 47% yield.

NMR(CDCL$_3$) δ: 7.5(1H, s), 6.96(1H, s), 5.08(1H, s), 4.67(1H, d; J=4.5 Hz). 4.4(1H, t), 4.1(1H, m), 3.97(3H, s), 3.9(1H, dd), 1.33(3H, s), 0.8(6H, d).

High Resolution MS: M+H=587.2226 (Δm=2.1 mDa).

Intermediate 17

A solution of Intermediate 16 (185 mg, 0.3153 mmol) and ammonium hydrogen difluoride (72 mg, 1.26 mmol) in dry (mol sieves) DMF (1.2 ml) and 1-methyl-2-pyrrolidinone (0.49 ml) was stirred at room temperature for 24 hours. The reaction mixture was filtered and evaporated to dryness to give, after flash column chromatography (20–50% ethyl acetate/hexanes), 114.5 mg of Intermediate 17 in 76.5% yield.

NMR(CDCL$_3$) δ: 7.48(1H, s), 6.96(1H, s), 5.2(1H, s), 4.7((1H, d; J=4.5 Hz), 4.3(1H, m), 4.15(2H, m), 3.98(3H, s), 1.33(3H, s).

High Resolution MS: M+H=473.1393 (Δm=−1.1 mDa).

EXAMPLE 3

A solution of Intermediate 17 (107.5 mg, 0.2275 mmol) in m-cresol (0.7 ml) was heated at 47° C. for 4 hours. The solution was then cooled to room temperature and diluted with ether. A solution of sodium bicarbonate (19.1 mg, 0.2275 mmol) in water (10 ml) was added and the organic phase removed. The aqueous phase was washed with ether and freeze-dried to give 47.8 mg of product in 64% yield.

NMR(D$_2$O) δ: 7.68(1H, s), 5.18(1H, d; J=4.5 Hz), 4.88 (1H, s), 4.35(1H, m), 4.2(1H, t), 4.08(1H, dd), 3.97(3H, s), 1.66(3H, s).

High Resolution MS: M−H=305.0443 (Δm=−1 mDa)

The activity of the present compounds is demonstrated by the following pharmacological test procedures.

Representative compounds according to the present invention were tested in a microbiological assay in combination with the penicillin antibiotic piperacillin. The enhanced combined synergestic antibacterial activity is representative of the β-lactamase inhibitory properties of the compounds of the present invention. In these tests, minimum inhibitory properties (MIC's) are determined in broth using several two-fold dilutions with a 1:1 ratio of piperacillin to inhibitor (N. A. Kuck, N. V. Jacobus, P. J. Peterson, W. J. Weiss, and R. T. Testa, *Antibiotic Agents and Chemotherapy*, 33:1964–1969 (1989)). The results are set forth in Table 1.

Representative compounds of the present invention were also tested against a comercally available inhibitor, tazobactam, to determine inhibition of the AmpC and TEM-1 β-lactamase enzymes. IC$_{50}$ values were determined spectrophotometrically using a 10 minute preincubation of enzyme with inhibitor at 25° C. before addition of nitrocefin as a substrate. The results are also set forth in Table 1.

TABLE 1

| Compound | IC$_{50}$ (nM) | | MIC (μg/ml; 1:1[d]) | |
|---|---|---|---|---|
| | TEM-1 | AmpC | E. coli[a] | S. marcescens[b] |
| Example 1 | 6 | 360 | 2[c] | 16[e] |
| Example 2 (cis) | 19 | 270 | 4 | 8 |
| Example 2 (trans) | 74 | 280 | 16 | 4 |
| Example 3 | 64 | 280 | 8 | 16 |
| Tazobactam | 60 | 47,700 | 2 | 32 |
| Piperacillin | | >64 | | 32 |

[a]GC6265, TEM-1 (Class A); [b]GC4132, AmpC (Class C); [c]GC2847, TEM-1 (Class A); [d]piperacillin:inhibitor ratio; [e]GC2894; AmpC (Class C).

When the present compounds are employed for the above utility, they may be combined with one or more pharmaceutically acceptable carriers, e.g., solvents, dilutents, etc., and may be administered parentally in the form of sterile injectable solutions or suspensions containing from about 0.05% to about 5% suspending agent in an isotonic medium. Such pharmaceutical preparations may contain from about 0.05% to about 90% of the active ingredient in combination with the carrier, more usually between about 5% and about 60% by weight.

The effective dosage of active ingredient employed may vary depending upon the particular compound used, the mode of administration and the severity of the condition being treated. However, in general, satisfactory results are obtained when the compounds of the invention are administered at a daily dosage of from about 2 to 100 mg/kg of animal body weight, preferably given in divided doses two to four times a day. In general, the total daily dose is from about 100 mg to about 750 mg, preferably from about 100 to about 500 kg. Dosage forms suitable for internal use include from about 100 to 750 mg of active compound in intimate admixture with a liquid pharmaceutically acceptable carrier. This dosage regimen may be adjusted to provide the optimal therapeutic response. For example, several divided doses may be administered daily or the dose may be proportionally reduced as indicated by the therapeutic situation. A practical advantage is that the present compounds may be administered by intravenous, intramuscular or subcutaneous rates. Liquid carriers include sterile water, polyethylene glycols, non-conic-surfactants and edible oils such as corn, peanut, and sesame oils as appropriate. Adjuvants normally employed in the preparation of pharmaceutical preparations may be used, such as vitamin E, ascorbic acid, BHT and BHA.

The present compounds may be administered parentally or intraperitoneally. Solutions or suspension of these active compounds can be prepared in water suitably mixed with a surfactant such as hydroxypropylcellulose. Dispersions can be prepared in glycerol, liquid polyethylene glycols and mixtures thereof in oils. Under ordinary conditions of storage and use, these preparations contain a preservative to prevent the growth of microorganisms.

The pharmaceutical forms suitable for injection use include sterile aqueous solutions and sterile powders for the preparation of sterile injectable solutions or dispensors. In all cases, the forms must be sterile and must be fluid so that easy syringability exists. It must be stable under conditions of manufacture and storage and must be preserved against the contaminating action of microorganisms. The carrier may be a solvent or dispension medium containing, e.g., water, ethanol, apolyl (e.g., glyceol, propylene glycol and liquid polyethylene glycol) and vegetable oils.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of formulae I or II:

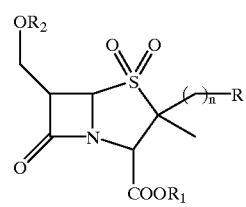

I

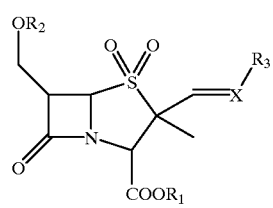

II wherein n is 0 or 1 and when n=1, R is hydroxy, halogen, carbamoyl, alkoxy, or a 5 or 6 membered heterocyclic ring containing one to three nitrogen atoms and optionally one oxygen or sulfur atom;

when n=0, R is a cyano group;

X is CH or N;

$R_3$ is cyano, methoxy or acetamido $R_1$ is hydrogen, alkyl, or alkoxycarbonyloxyalkyl, sodium, potassium or tetraalkylammonium; and $R_2$ is hydrogen, carbamoyl or an amino acid residue; or pharmaceutically acceptable salts thereof.

2. A compound according to claim 1 wherein n is 1' and R is 1,2,3-triazole, isoxazole, imidazole or pyridine; $R_1$ is sodium; and $R_2$ is hydrogen; or pharmaceutically acceptable salts thereof.

3. A compound according to claim 1 which is (2S, 3S, 5R, 6R)-6-Hydroxymethyl-3-methyl-4,4,7-trioxo-3-[1,2,3]triazol-1-ylmethyl-4-lambda(6)-thia-1-azabicyclo[3.2.0]heptane-2-carboxylic acid.

4. A compound according to claim 1 which is (2S, 3R, 5R, 6R)-6-Hydroxymethyl-3-(methoxyamino-methyl)-3-methyl-4,4,7-trioxo-4-lambda(6)-thia-1-aza-bicyclo[3.2.0]heptane-2-carboxylic acid.

5. A compound according to claim 1 which is (Z)-(2S, 3S, 5R, 6R)-6-Hydroxymethyl-3-methyl-3-(3-nitrilo-propenyl)-4,4,7-trioxo-4-lambda(6)-thia-1-aza-bicyclo[3.2.0]heptane-2-carboxylic acid.

6. A compound according to claim 1 which is (E)-(2S, 3S, 5R, 6R)-6-Hydroxymethyl-3-methyl-3-(3-nitrilo-propenyl)-4,4,7-trioxo-4-lambda(6)-thia-1-aza-bicyclo[3.2.0]heptane-2-carboxylic acid.

7. A pharmaceutical composition comprising a compound having formulae I or II:

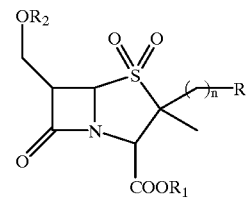

I

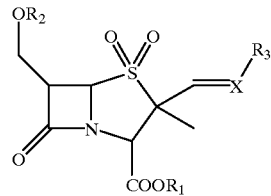

II wherein n is 0 or 1 and when n=1, R is hydroxy, halogen, carbamoyl, alkoxy, or a 5 or 6 membered heterocyclic ring containing one to three nitrogen atoms and optionally one oxygen or sulfur atom;

when n=0, R is a cyano group;

X is CH or N;

$R_3$ is cyano, methoxy or acetamido $R_1$ is hydrogen, alkyl, or alkoxycarbonyloxyalky, sodium, potassium or tetraalkylammonium; and $R_2$ is hydrogen, carbamoyl or an amino acid residue; or pharmaceutically acceptable salts thereof.

8. A method of controlling bacterial infections in a host in need of such therapy comprising administering to said host a compound of formulae I or II

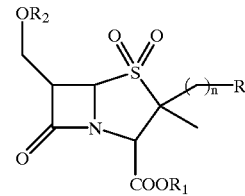

I

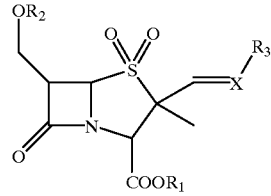

II wherein n is 0 or 1 and when n=1, R is hydroxy, halogen, carbamoyl, alkoxy, or a 5 or 6 membered heterocyclic ring containing one to three nitrogen atoms and optionally one oxygen or sulfur atom;

when n=0, R is a cyano group;

X is CH or N;

$R_3$ is cyano, methoxy or acetamido;

$R_1$ is hydrogen, alkyl, or alkoxycarbonyloxyalkyl, sodium, potassium or tetraalkylammonium; and $R_2$ is hydrogen, carbamoyl or an amino acid residue; or pharmaceutically acceptable salts thereof.

\* \* \* \* \*